US010322257B2

(12) United States Patent
DiMatteo et al.

(10) Patent No.: US 10,322,257 B2
(45) Date of Patent: Jun. 18, 2019

(54) HUMIDIFIER ASSEMBLY AND METHOD OF PROVIDING MOISTURE TO SUPPLIED GAS IN A PRESSURE SUPPORT SYSTEM

(71) Applicant: KONINKLIJKE PHILIPS N.V., Eindhoven (NL)

(72) Inventors: Mark William DiMatteo, Irwin, PA (US); Mark Wayne Barclay, Saxonburg, PA (US); John Raymond Pujol, Murrysville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 761 days.

(21) Appl. No.: 14/897,110

(22) PCT Filed: Jun. 30, 2014

(86) PCT No.: PCT/IB2014/062723
§ 371 (c)(1),
(2) Date: Dec. 9, 2015

(87) PCT Pub. No.: WO2014/207730
PCT Pub. Date: Dec. 31, 2014

(65) Prior Publication Data
US 2016/0129212 A1    May 12, 2016

Related U.S. Application Data

(60) Provisional application No. 61/972,239, filed on Mar. 29, 2014, provisional application No. 61/840,684, filed on Jun. 28, 2013.

(51) Int. Cl.
*A61M 16/16* (2006.01)
*A61M 16/06* (2006.01)
(Continued)

(52) U.S. Cl.
CPC ........ *A61M 16/165* (2014.02); *A61M 16/024* (2017.08); *A61M 16/0816* (2013.01);
(Continued)

(58) Field of Classification Search
CPC .............. A61M 16/00; A61M 16/0051; A61M 16/0057; A61M 16/0066; A61M 16/08;
(Continued)

(56) References Cited

U.S. PATENT DOCUMENTS 2,405,494 A * 8/1946 Dupuy ............... F24F 6/12
                                          261/120
3,526,226 A * 9/1970 Stern ................. A61M 16/06
                                          128/203.27
(Continued)

FOREIGN PATENT DOCUMENTS

CN    2899822 Y    5/2007
CN    202961442 U  6/2013
(Continued)

*Primary Examiner* — Jan Christopher L Merene
*Assistant Examiner* — Joseph D. Boecker

(57) ABSTRACT

A humidifier assembly (100, 100-1) includes a reservoir (120), an inlet structure (112, 112-1) leading into the reservoir and an outlet structure (114, 114-1) leading out of the reservoir, and a conduit element (130, 130-1) having a first end (131, 131-1), a body portion (132, 132-1), and a second end (133, 133-1). The first end is fluidly coupled to at least one of the inlet structure and the outlet structure The humidifier assembly additionally includes a float assembly (140, 140-1) coupled to the second end of the conduit element. The float assembly is structured to float on water held by the reservoir. The float assembly has a number of apertures (153, 153-1) structured to be in fluid communication with the outlet structure.

14 Claims, 19 Drawing Sheets

(51) Int. Cl.
*A61M 16/08* (2006.01)
*A61M 16/00* (2006.01)

(52) U.S. Cl.
CPC ......... *A61M 16/16* (2013.01); *A61M 16/0069* (2014.02); *A61M 16/08* (2013.01); *A61M 16/161* (2014.02); *A61M 2016/0039* (2013.01); *A61M 2205/21* (2013.01); *A61M 2205/3368* (2013.01); *A61M 2205/502* (2013.01)

(58) Field of Classification Search
CPC ............ A61M 16/0816; A61M 16/109; A61M 16/14; A61M 16/16; A61M 16/161; A61M 16/165; A61M 16/167; A61M 2205/21; A61M 2205/215; F24F 2006/008
See application file for complete search history.

(56) References Cited

U.S. PATENT DOCUMENTS

| | | | |
|---|---|---|---|
| 3,778,978 A | 12/1973 | Matsushita | |
| 3,865,106 A * | 2/1975 | Palush | A61M 16/08 128/200.18 |
| 4,192,836 A | 3/1980 | Bartscher et al. | |
| 4,304,739 A * | 12/1981 | Thorne | B01D 47/021 261/120 |
| 4,461,735 A | 7/1984 | Wirt | |
| 4,793,835 A * | 12/1988 | Rylander | F24F 3/16 261/120 |
| 5,148,802 A | 9/1992 | Sanders et al. | |
| 5,313,937 A | 5/1994 | Zdrojkowski | |
| 5,433,193 A | 7/1995 | Sanders et al. | |
| 5,445,143 A | 8/1995 | Sims | |
| 5,632,269 A | 5/1997 | Zdrojkowski | |
| 5,803,065 A | 9/1998 | Zdrojkowski et al. | |
| 6,029,664 A | 2/2000 | Zdrojkowski et al. | |
| 6,539,940 B2 | 4/2003 | Zdrojkowski et al. | |
| 6,626,175 B2 | 9/2003 | Jafari et al. | |
| 7,011,091 B2 | 3/2006 | Hill et al. | |
| 2004/0040599 A1* | 3/2004 | Payne | B29C 44/0415 137/409 |
| 2005/0022810 A1 | 2/2005 | Moore et al. | |
| 2007/0132117 A1* | 6/2007 | Pujol | A61M 16/16 261/119.1 |
| 2007/0144198 A1* | 6/2007 | Lee | F24F 13/222 62/291 |
| 2008/0054500 A1 | 3/2008 | Bradley | |
| 2008/0105257 A1 | 5/2008 | Klasek et al. | |
| 2010/0224184 A1 | 9/2010 | Ahlmen et al. | |
| 2012/0012186 A1 | 1/2012 | Tantra et al. | |

FOREIGN PATENT DOCUMENTS

| | | |
|---|---|---|
| EP | 2119466 A1 | 11/2009 |
| GB | 1129194 A | 10/1968 |
| RU | 2104049 C1 | 2/1998 |
| WO | 2003004938 A1 | 1/2003 |

\* cited by examiner

HUMIDIFIER ASSEMBLY AND METHOD OF PROVIDING MOISTURE TO SUPPLIED GAS IN A PRESSURE SUPPORT SYSTEM

CROSS-REFERENCE TO PRIOR APPLICATIONS

This application is the U.S. National Phase application under 35 U.S.C. § 371 of International Application Serial No. PCT/IB2014/062723, filed on Jun. 30, 2014, which claims the benefit of U.S. Application Ser. No. 61/840,684, filed on Jun. 28, 2013 and U.S. Application Ser. No. 61/972,239, filed on Mar. 29, 2014. These applications are hereby incorporated by reference herein.

BACKGROUND OF THE INVENTION

1. Field of the Invention

The present invention relates to airway pressure support systems, and, more particularly, to humidifiers provided in airway pressure support systems.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether OSA, central, or mixed, which is a combination of OSA and central, is defined as the complete or near cessation of breathing, for example a 90% or greater reduction in peak respiratory airflow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring. Thus, in diagnosing a patient with a breathing disorder, such as OSA, central apneas, or UARS, it is important to detect accurately the occurrence of apneas and hypopneas of the patient.

It is well known to treat sleep disordered breathing by applying a positive air pressure (PAP) to the patient's airway. This positive pressure effectively "splints" the airway, thereby maintaining an open passage to the lungs. In one type of PAP therapy, known as continuous positive air pressure (CPAP), the pressure of gas delivered to the patient is constant throughout the patient's breathing cycle. It is also known to provide a positive pressure therapy in which the pressure of gas delivered to the patient varies with the patient's breathing cycle, or varies with the patient's effort, to increase the comfort to the patient. This pressure support technique is referred to as bi-level pressure support, in which the inspiratory positive airway pressure (IPAP) delivered to the patient is higher than the expiratory positive airway pressure (EPAP).

Humidifiers are frequently provided between or integral with a PAP machine and the user interface in order to humidify the otherwise relatively-dry compressed air generated by the PAP machine. Typically, humidifiers can be categorized as passover types or non-passover types. In a passover type of humidifier, water is contained in a reservoir that may or may not be heated. While the water is allowed to evaporate to produce vapor within the reservoir, breathing gas is passed over the surface of the water.

In current PAP machines, during misuse conditions, such as when the PAP machine is dropped or is rotated, water from the reservoir can enter the main housing of the PAP machine and potentially cause damage thereto. Furthermore, to account for this potential of water ingress back into the main housing of the PAP machine, the reservoir needs to be larger than what is required to deliver therapy, so that there is always sufficient water for humidification. This adds weight to the PAP machine and makes it more difficult to transport.

There is thus room for improvement in airway pressure support systems including humidifiers.

SUMMARY OF THE INVENTION

In one embodiment, a humidifier assembly is provided that includes a reservoir, an inlet structure leading into the reservoir and an outlet structure leading out of the reservoir, and a conduit element having a first end, a body portion, and a second end. The first end is fluidly coupled to at least one of the inlet structure and the outlet structure. The humidifier assembly additionally includes a float assembly coupled to the second end of the conduit element. The float assembly is structured to float on water held by the reservoir. The float assembly has a number of apertures structured to be in fluid communication with the interior of the reservoir and the outlet structure.

In another embodiment, a method of providing moisture to supplied gas in a pressure support system includes the step of generating a flow of breathing gas with a gas flow generator. The gas flow generator is adapted to be coupled to a humidifier assembly that includes a reservoir adapted to contain water, a conduit element and a float assembly coupled to the conduit element and having a number of apertures, the float assembly being adapted to float on the water. The method further includes the step of passing the breathing gas through the conduit element and through the number of apertures of the float assembly, passing the breathing gas over the water, and delivering the breathing gas from the humidifier assembly to a patient via a patient circuit coupled to the reservoir.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
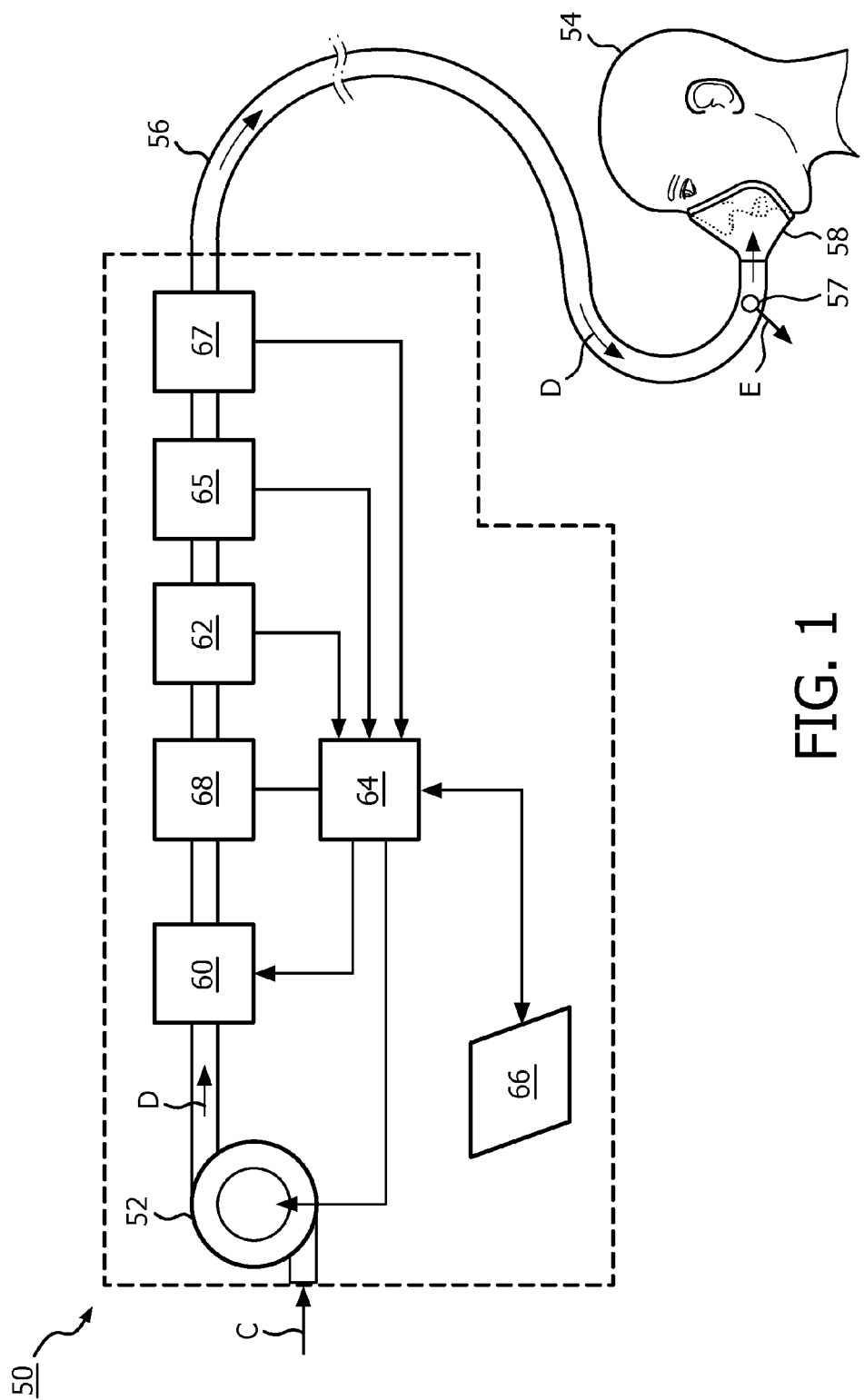
FIG. 1 is a schematic diagram of a pressure support system according to one particular, non-limiting embodiment in which the present invention in its various embodiments may be implemented.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality).

FIG. 1 is a schematic diagram of a pressure support system 50 according to one particular, non-limiting embodiment in which the present invention in its various embodiments may be implemented. Referring to FIG. 1, pressure support system 50 includes a gas flow generator 52, such as a blower used in a conventional CPAP or bi-level pressure support device, which receives breathing gas, generally indicated by arrow C, from any suitable source, e.g., a pressurized tank of oxygen or air, the ambient atmosphere, or a combination thereof. Gas flow generator 52 generates a flow of breathing gas, such as air, oxygen, or a mixture thereof, for delivery to an airway of a patient 54 at relatively higher and lower pressures, i.e., generally equal to or above ambient atmospheric pressure. In the exemplary embodiment, gas flow generator 52 is capable of providing a flow of breathing gas ranging in pressure from 3-30 cmH$_2$O. The pressurized flow of breathing gas, generally indicated by arrow D from gas flow generator 52, is delivered via a delivery tube 56 to a breathing mask or patient interface 58 of any known construction, which is typically worn by or otherwise attached to patient 54 to communicate the flow of breathing gas to the airway of patient 54. Delivery tube 56 and patient interface device 58 are typically collectively referred to as a patient circuit.

Pressure support system 50 shown in FIG. 1 is what is known as a single-limb system, meaning that the patient circuit includes only delivery tube 56 connecting patient 54 to pressure support system 50. As such, an exhaust vent 57 is provided in delivery tube 56 for venting exhaled gases from the system as indicated by arrow E. It should be noted that exhaust vent 57 can be provided at other locations in addition to or instead of in delivery tube 56, such as in patient interface device 58. It should also be understood that exhaust vent 57 can have a wide variety of configurations depending on the desired manner in which gas is to be vented from pressure support system 50.

The present invention also contemplates that pressure support system 50 can be a two-limb system, having a delivery tube and an exhaust tube connected to patient 54. In a two-limb system (also referred to as a dual-limb system), the exhaust tube carries exhaust gas from patient 54 and includes an exhaust valve at the end distal from patient 54. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 1, patient interface 58 is a nasal/oral mask. It is to be understood, however, that patient interface 58 can include a nasal mask, nasal pillows, a tracheal tube, an endotracheal tube, or any other device that provides a suitable gas flow communicating function. Also, for purposes of the present invention, the phrase "patient interface" can include delivery tube 56 and any other structures that couple the source of pressurized breathing gas to patient 54.

In the illustrated embodiment, pressure support system 50 includes a pressure controller in the form of a valve 60 provided in delivery tube 56. Valve 60 controls the pressure of the flow of breathing gas from flow generator 52 that is delivered to patient 54. For present purposes, flow generator 52 and valve 60 are collectively referred to as a pressure generating system because they act in concert to control the pressure and/or flow of gas delivered to patient 54. However, it should be apparent that other techniques for controlling the pressure of the gas delivered to patient 54, such as varying the blower speed of flow generator 52, either alone or in combination with a pressure control valve, are contemplated by the present invention. Thus, valve 60 is optional depending on the technique used to control the pressure of the flow of breathing gas delivered to patient 54. If valve 60 is eliminated, the pressure generating system corresponds to flow generator 52 alone, and the pressure of gas in the patient circuit is controlled, for example, by controlling the motor speed of flow generator 52.

Pressure support system 50 further includes a flow sensor 62 that measures the flow of the breathing gas within delivery tube 56. In the particular embodiment shown in FIG. 1, flow sensor 62 is interposed in line with delivery tube 56, most preferably downstream of valve 60. Flow sensor 62 generates a flow signal, $Q_{measured}$, that is provided to a controller 64 and is used by controller 64 to determine the flow of gas at patient 54 ($Q_{patient}$).

Techniques for calculating $Q_{patient}$ based on $Q_{measured}$ are well known, and take into consideration the pressure drop of the patient circuit, known leaks from the system, i.e., the intentional exhausting of gas from the circuit as indicated by arrow E in FIG. 1, and unknown leaks from the system, such as leaks at the mask/patient interface. The present invention contemplates using any known or hereafter developed technique for calculating leak flow $Q_{leak}$, and using this determination in calculating $Q_{patient}$ based on $Q_{measured}$. Examples techniques are taught by U.S. Pat. Nos. 5,148,802; 5,313,937; 5,433,193; 5,632,269; 5,803,065; 6,029,664; 6,539,940; 6,626,175; and 7,011,091, the contents of each of which are incorporated by reference into the present invention.

Of course, other techniques for measuring the respiratory flow of patient 54 are contemplated by the present invention, such as, without limitation, measuring the flow directly at patient 54 or at other locations along delivery tube 56, measuring patient flow based on the operation of flow generator 52, and measuring patient flow using a flow sensor upstream of valve 60.

In the illustrated embodiment, pressure support system 50 also includes a temperature sensor 65 operatively coupled to delivery tube 56 for detecting the temperature of the gas stream output by pressure support system 50, and a humidity sensor 67 operatively coupled to delivery tube 56 for detecting the humidity of the gas stream output by pressure support system 50. Temperature sensor 65 and humidity sensor 67 are each operatively coupled to controller 64. In the embodiment shown, temperature sensor 65 and humidity sensor 67 are provided within the main housing of pressure support system 50. Alternatively, either or both of temperature sensor 65 and humidity sensor 67 may be provided in or coupled to the patient circuit.

Controller 64 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of pressure support system 50, including automatically controlling humidity as described in greater detail herein.

An input/output device 66 is provided for setting various parameters used by pressure support system 50, as well as for displaying and outputting information and data to a user, such as a clinician or caregiver.

In the illustrated, non-limiting embodiment of the present invention, pressure support system 50 essentially functions as a CPAP pressure support system, and, therefore, includes all of the capabilities necessary in such systems in order to provide appropriate CPAP pressure levels to patient 54. This includes receiving the necessary parameters, via input commands, signals, instructions or other information, for providing appropriate CPAP pressure, such as maximum and minimum CPAP pressure settings. It should be understood that this is meant to be exemplary only, and that other pressure support methodologies, including, but not limited to, BiPAP AutoSV, AVAPS, Auto CPAP, and BiPAP Auto, are within the scope of the present invention.

Finally, in the illustrated embodiment, pressure support system 50 includes a humidifier 68 provided in the main housing of pressure support system 50. Alternatively, humidifier 68 may be separate from and located external to the main housing. Humidifier 68 is coupled to and controlled by controller 64, and further improves patient comfort by providing moisture in the supplied gas. In the exemplary embodiment, described in detail herein, humidifier 68 is a passover type humidifier.

Figure 2:
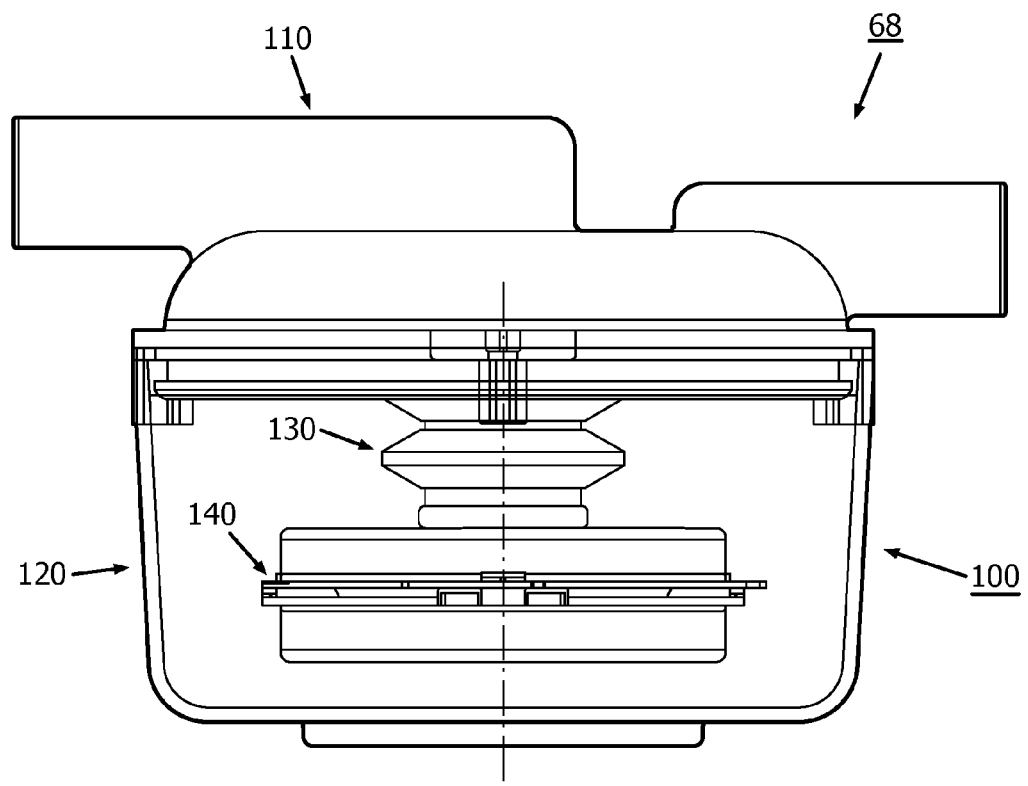
FIG. 2 is a front elevational view of a humidifier assembly in accordance with an exemplary embodiment of the disclosed concept.
Figure 3:
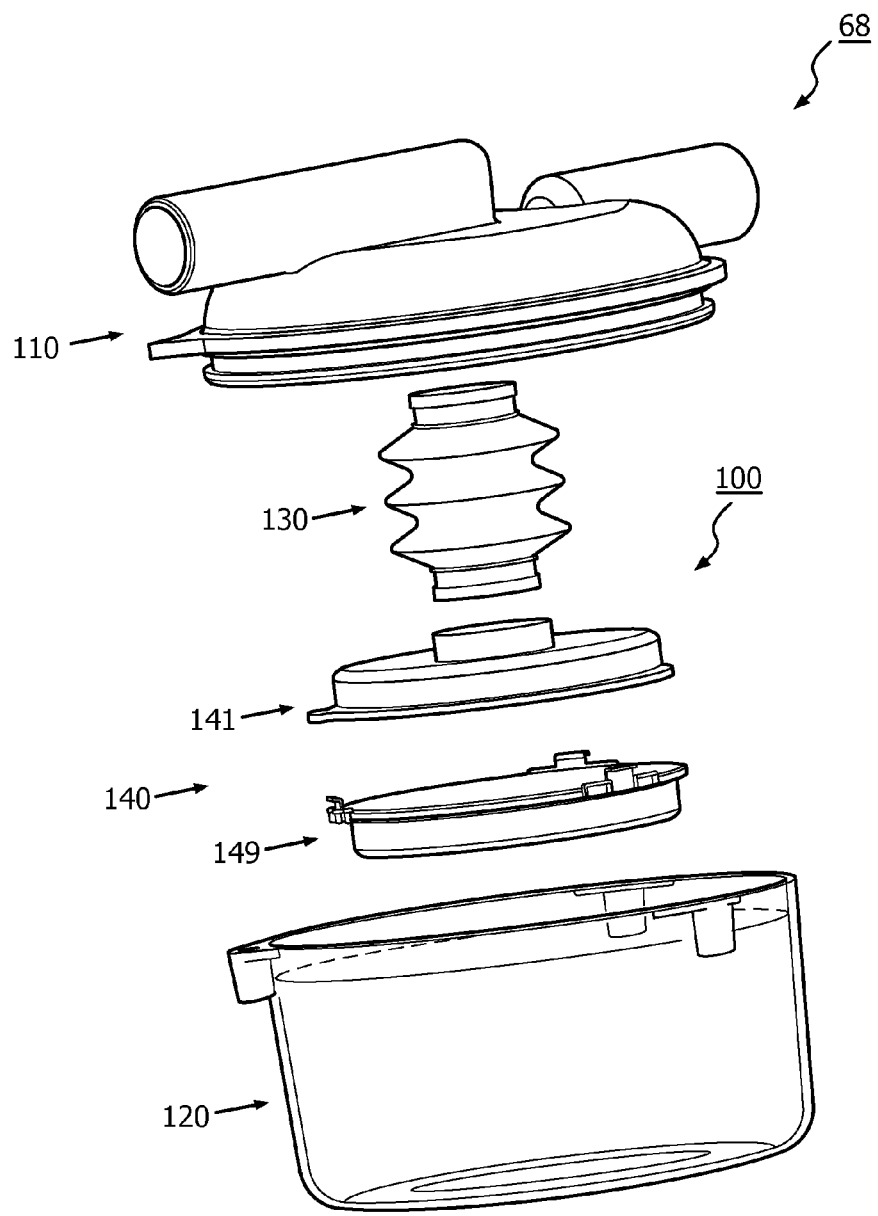
FIG. 3 is an exploded view of the humidifier assembly of FIG. 2.

FIG. 2 is a front elevational view and FIG. 3 is an exploded view of a humidifier assembly 100 according to an exemplary embodiment of the present invention that may be used to implement humidifier 68 of pressure support system 50. As seen in FIGS. 2 and 3, humidifier assembly 100 includes an adaptor 110, a reservoir 120 for holding water therein, an inlet tube 130, and a float assembly 140, each of which is described in more detail below.

Figure 4:
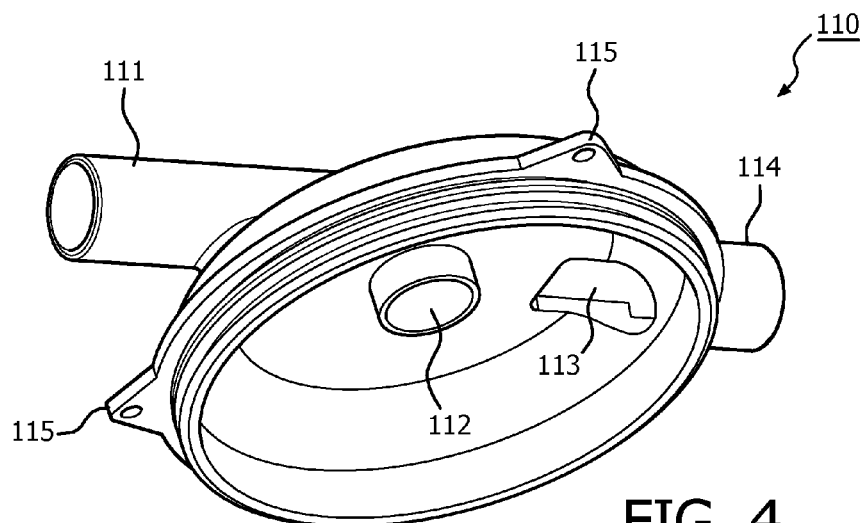
FIG. 4 is a bottom isometric view of an adaptor of the humidifier assembly of FIG. 2.

As seen in FIG. 4, which is a bottom isometric view of adaptor 110, adaptor 110 includes an inlet end 111 through which air from gas flow generator 52 can enter humidifier assembly 100. Adaptor 110 further includes an inlet port 112 in fluid communication with the inlet end 11, an outlet aperture 113, an outlet end 114, and a plurality of apertures 115. In operation, air flows from inlet end 111 to inlet port 112, which is structured to be coupled to inlet tube 130. Inlet port 112 may be coupled to inlet tube 130 by any suitable mechanism known in the art (e.g., without limitation, a press fit). Air, after passing over water in reservoir 120 and becoming humidified, exits humidifier assembly 100 through outlet aperture 113 and flows to outlet end 114, which is structured to be coupled to delivery tube 56. Although adaptor 110 includes outlet aperture 113 which the air passes through, it is within the scope of the disclosed concept for an adaptor (not shown) to include another port or multiple ports similar to inlet port 112 for air to exit through.

Figure 5:
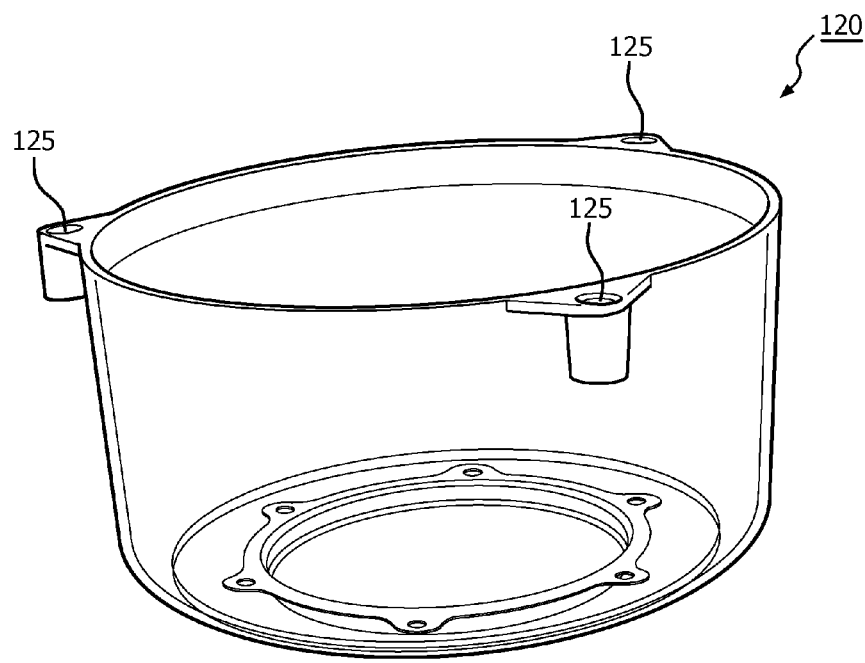
FIG. 5 is an isometric view of a reservoir of the humidifier assembly of FIG. 2.

Referring to FIGS. 4 and 5, adaptor 110 is structured to be coupled to reservoir 120, which, as noted elsewhere herein, holds water such that when breathing gas is passed over the water, the humidity of the breathing gas is increased. As seen in FIG. 5, reservoir 120 includes a plurality of apertures 125 that are structured to be aligned with apertures 115 when adaptor 110 is coupled to reservoir 120. In this manner, a plurality of pins (not shown) may be used to couple adaptor 110 to reservoir 120 at apertures 115,125. Although adaptor 110 has three apertures 115 and reservoir 120 has three apertures 125, the disclosed concept is not limited to three apertures and is not limited to the abovementioned coupling mechanism. For example and without limitation, an adaptor (not shown) may be coupled to a reservoir (not shown) by a threaded coupling or a tongue and groove mechanism.

Figure 6:
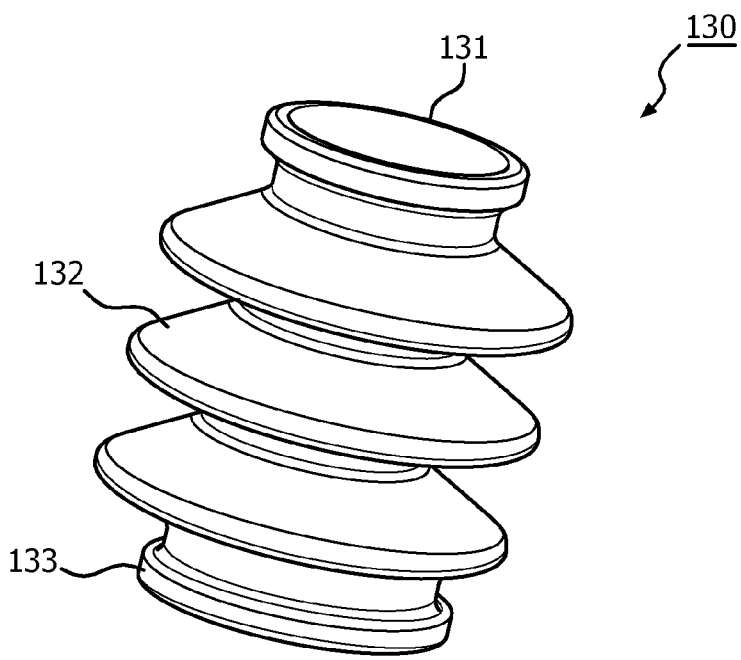
FIG. 6 is an isometric view of an inlet tube of the humidifier assembly of FIG. 2.
Figure 7:
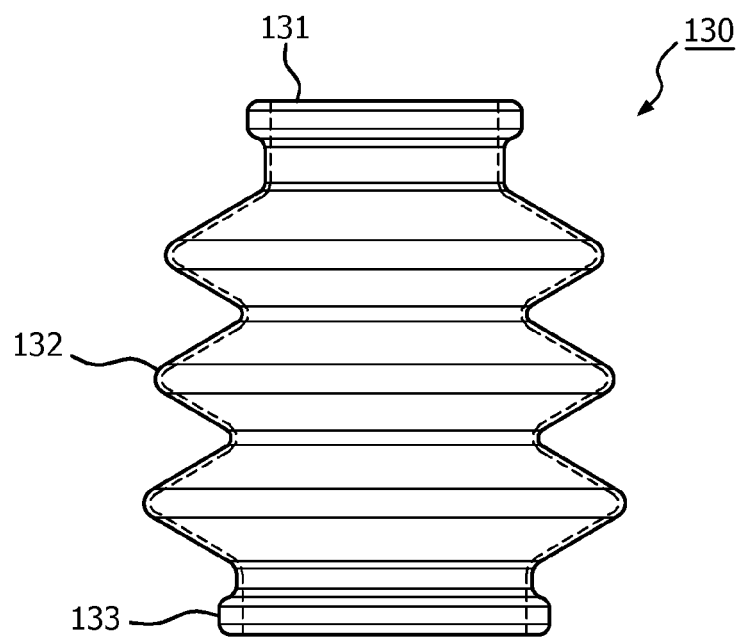
FIG. 7 is a front elevational view of the inlet tube of the humidifier assembly of FIG. 2.
Figure 8:
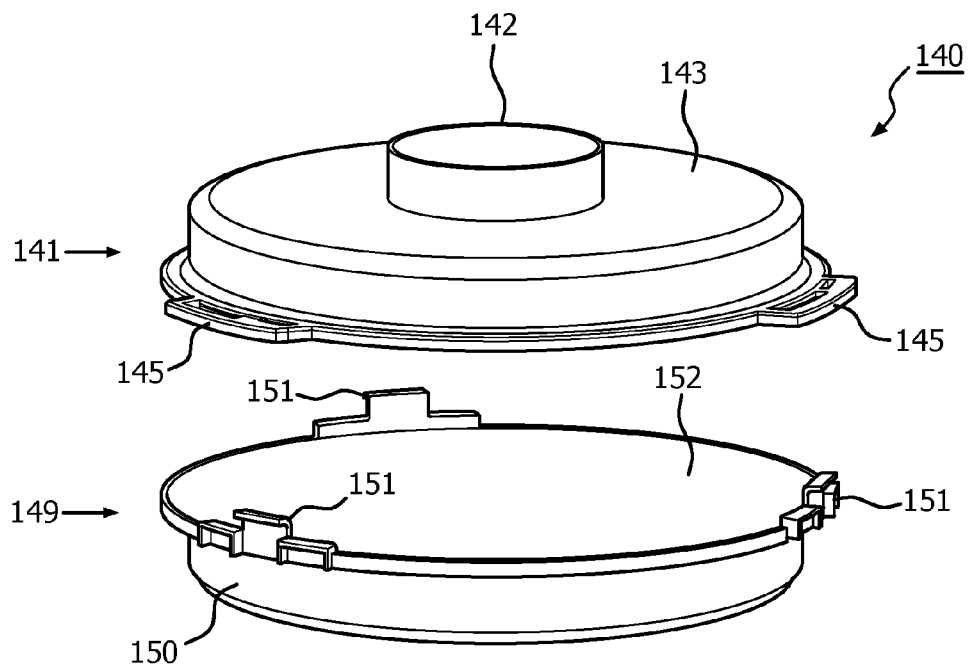
FIG. 8 is a partially exploded isometric view of a float assembly of the humidifier assembly of FIG. 2.
Figure 9:
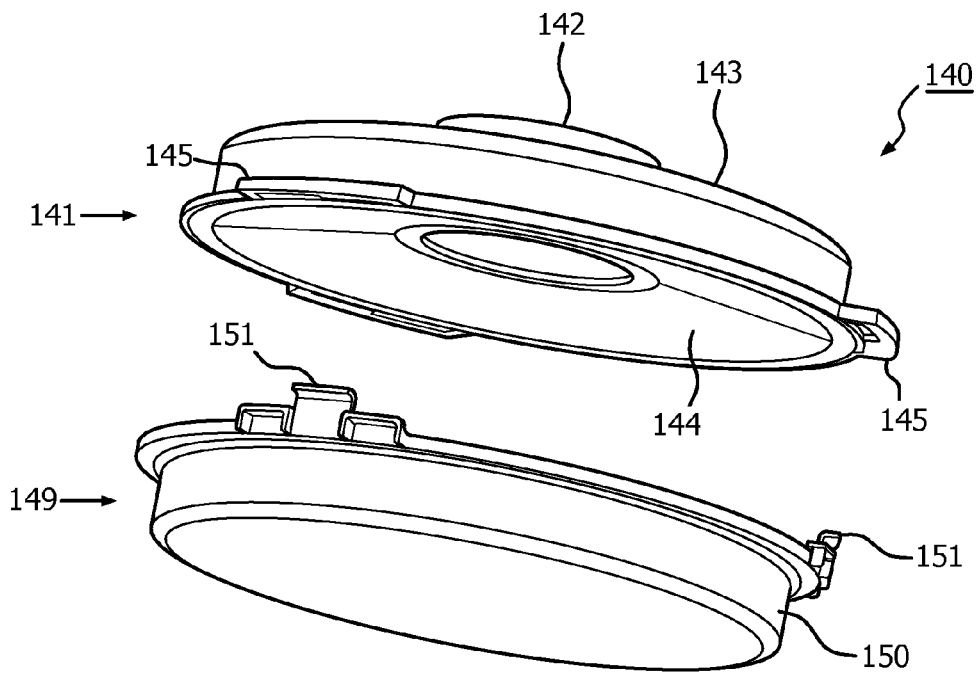
FIG. 9 is a another partially exploded isometric view of the float assembly of the humidifier assembly of FIG. 2.
Figure 10:
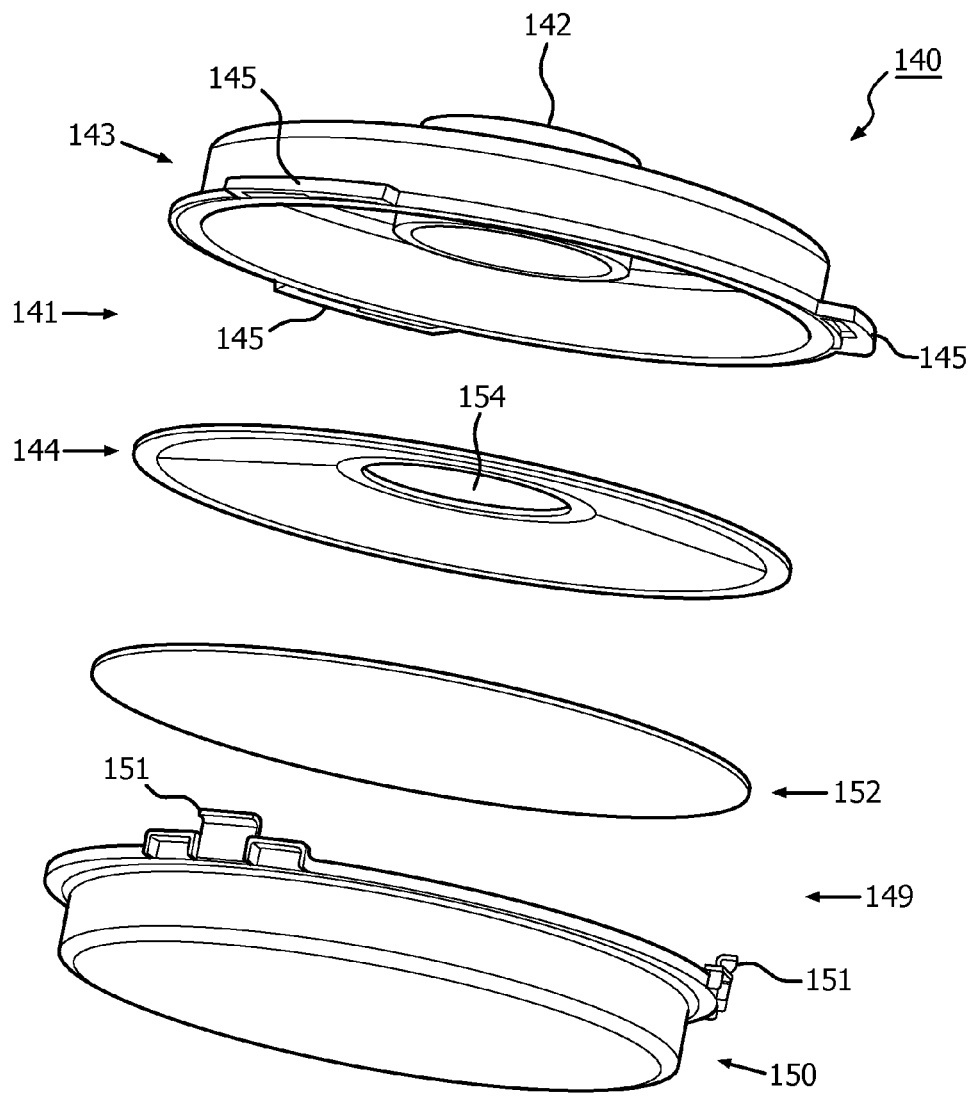
FIG. 10 is an exploded isometric view of the float assembly of the humidifier assembly of FIG. 2.
Figure 11:
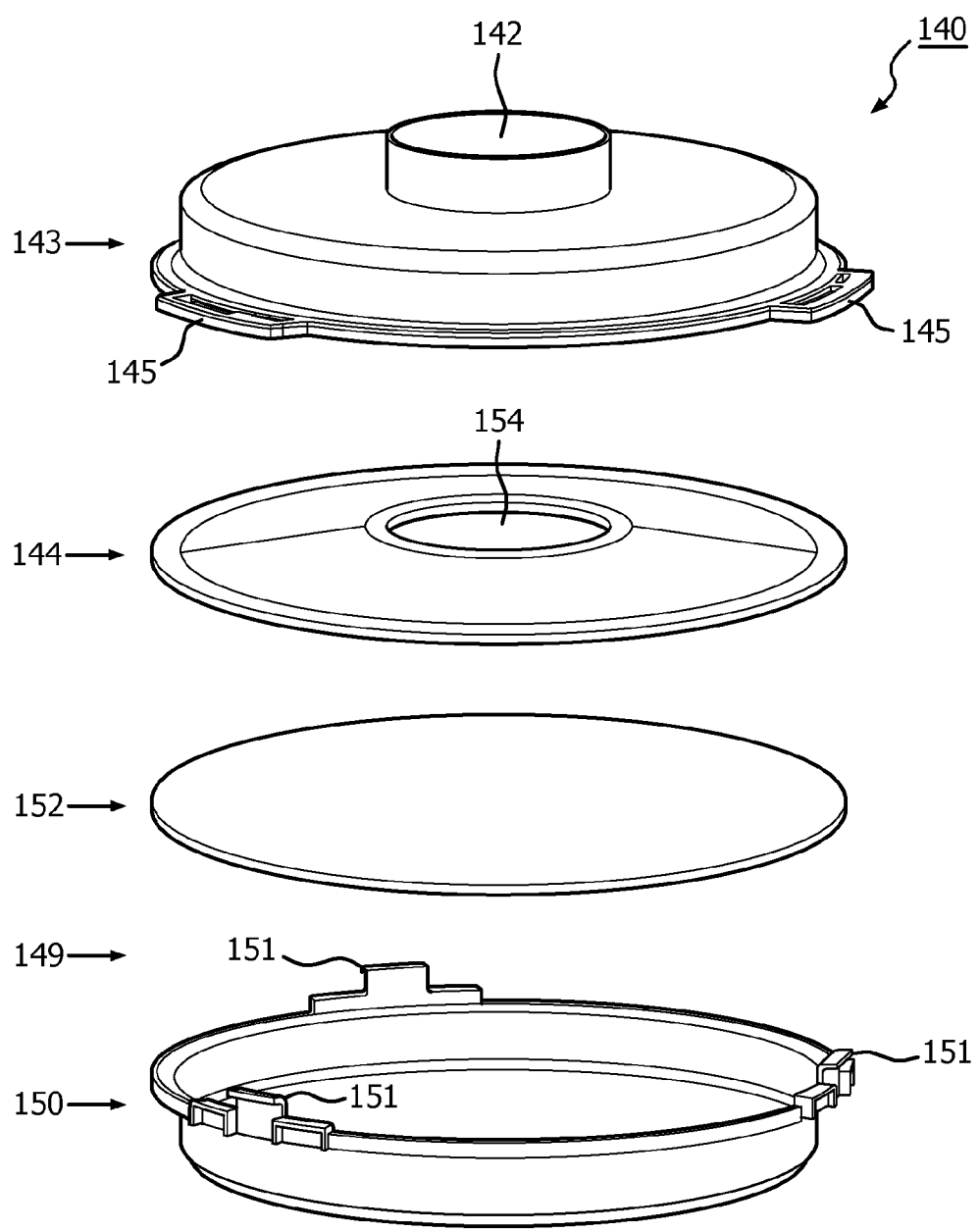
FIG. 11 is another exploded isometric view of the float assembly of the humidifier assembly of FIG. 2.

FIG. 6 is an isometric view and FIG. 7 is a front elevational view of inlet tube 130. As seen in FIGS. 6 and 7, inlet tube 130 includes a first end 131 that is structured to be coupled to inlet port 112 of adaptor 110. Inlet tube 130 further includes a flexible body portion 132 and a second end 133 that is structured to be coupled to float assembly 140. In the exemplary non-limiting embodiment, body portion 132 has a bellows shape, which allows it to readily expand and contract in a direction along the longitudinal axis of inlet tube 130. Body portion 132 is also able to readily bend in directions that are transverse to the longitudinal axis of inlet tube 130. The benefit of this functionality is described elsewhere herein.

Furthermore, while in the exemplary embodiment body portion 132 is provided with a bellows structure to allow it to readily expand or contract, it will be understood that it is within the scope of the disclosed concept for inlet tube 130 to have alternative structures. For example and without limitation, inlet tube 130 may be a flexible tube that does not include a bellows structure, but yet is able to bend depending on the position of float assembly 140, which, as described herein, depends on the water level within reservoir 120. Inlet tube 130 may be made of any material suitable to allow body portion 132 to expand and contract, and/or bend, such as, without limitation, a soft elastomeric material such as silicone rubber, a monomer, a polymer, or a mixture thereof.

Figure 12:
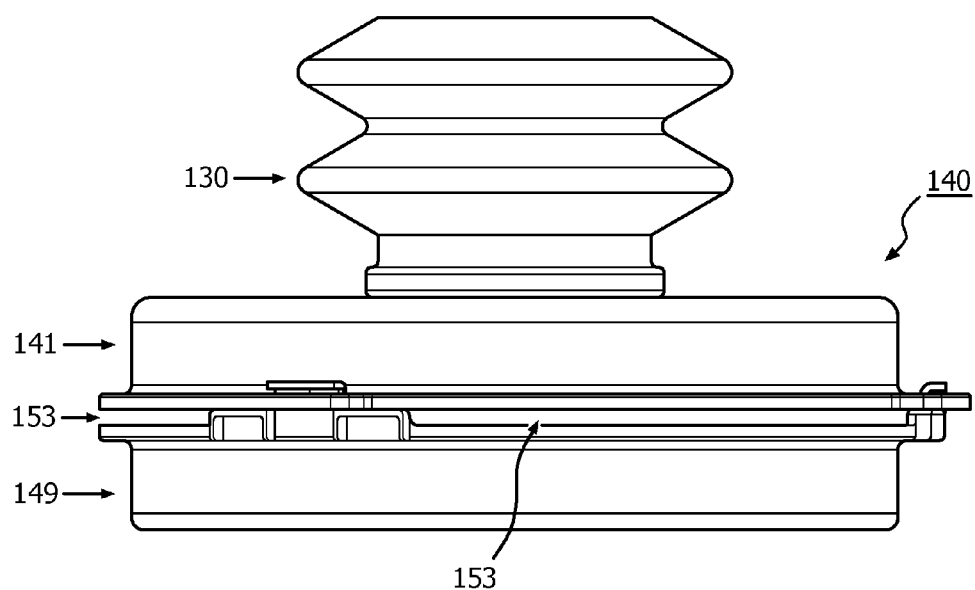
FIG. 12 is a front elevational view of the float assembly and a portion of the inlet tube of the humidifier assembly of FIG. 2.

FIGS. 8-11 are exploded isometric views of float assembly 140 according to the exemplary embodiment. FIG. 12 is a front elevational view showing inlet tube 130 coupled to float assembly 140. Float assembly 140 includes a first disc-shaped component 141 having an enclosure piece 143 and a base 144 having a central aperture 154 coupled to enclosure piece 143. Enclosure piece 143 includes an inlet port 142 that is structured to be coupled to end 133 of inlet tube 130. Inlet port 142 may be coupled to end 133 of inlet tube 130 by any suitable mechanism known in the art (e.g., without limitation, a press fit). Float assembly 140 further includes a second disc-shaped component 149 that is structured to be coupled to first component 141. Second component 149 includes an enclosure piece 152 and a base 150 (both being solid, without a central aperture) coupled to enclosure piece 152. When bases 144,150 are coupled to enclosure pieces 143,152, enclosed regions of air are formed therebetween. In this manner, float assembly 140 is adapted to float on the water contained in reservoir 120. Furthermore, bases 144,150 may be coupled to enclosure pieces 143,152 by any suitable mechanism known in the art (e.g., without limitation, snap-fit).

Bases 144,150 and enclosure pieces 143,152 can be constructed of materials suitable for floating on water, such as a material containing a monomer, polymer or mixture thereof, preferably being constructed of a thermoplastic material. In the exemplary embodiment, base 150 includes a plurality of tongues 151 that are structured to be received in a plurality of apertures 145 contained in enclosure piece 143. However, base 150 and enclosure piece 143 may have alternative structures to that described above for enabling a coupling between first component 141 and second component 149 of float assembly 140. Additionally, as seen in FIG. 12, when first component 141 of float assembly 140 is coupled to second component 149, a number of apertures 153 are formed therebetween which are structured to allow breathing gas to escape float assembly 140 and enter reservoir 120. In the exemplary embodiment, a plurality of apertures 153 (e.g., three) are formed.

In operation, air from gas flow generator 52 enters humidifier assembly 100 through inlet end 111 of adaptor 110. Air then flows through inlet tube 130 and enters float assembly 140 through inlet port 142 of first component 141. The air passes through central aperture 154 of base 144, at which point it is fanned out radially over enclosure piece 152. The air enters reservoir 120 through apertures 153 in float assembly 140. After being passed over water, air exits reservoir 120 through outlet aperture 113 in adaptor 110. Finally, the air passes through outlet end 114 of adaptor 110 and is delivered to patient 54.

Figure 13A:
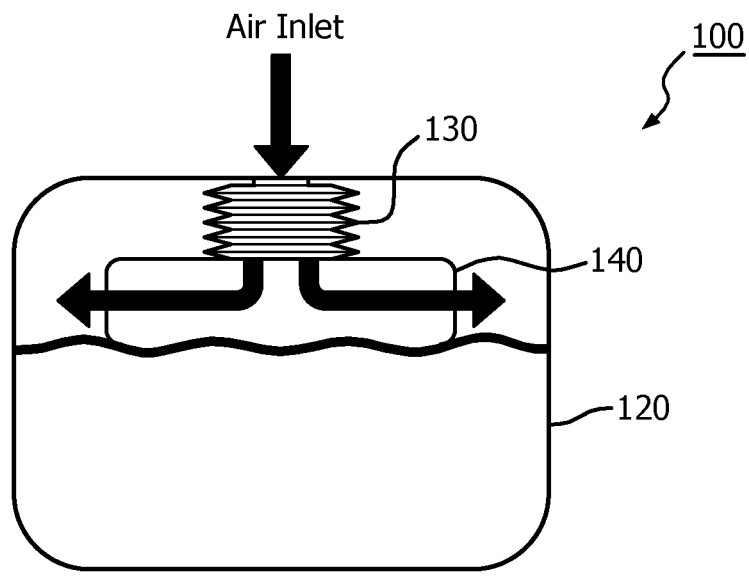
FIGS. 13A, 13B and 14 are schematic representations demonstrating operation of the humidifier assembly of FIG. 2.
Figure 13B:
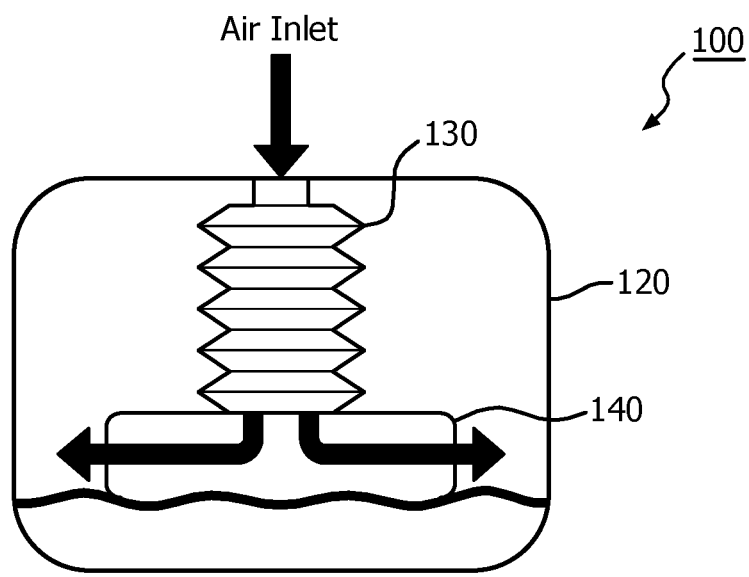

During use, float assembly 140 will remain at the same position with respect to the water level in reservoir 120 at all times. This is due to the fact that, as the water level in reservoir 120 changes (e.g., due to moisture being absorbed by the breathing gas or water being added by a user), body portion 132 of inlet tube 130 will expand or contract, and/or bend, as needed as float assembly 140 floats on top of the water. In this manner, air will enter reservoir 120 through apertures 153 at the same level with respect to the water. This is demonstrated schematically in FIGS. 13A and 13B. This advantageously results in a more consistent humidification output being delivered to patient 54.

Furthermore, float assembly 140 advantageously acts as a dispersion device (i.e., baffle) for the breathing gas passing through humidifier assembly 100. In particular, as the gas exits first component 141 through aperture 154, it will hit the top surface of enclosure piece 152 and be fanned out radially before exiting through apertures 153.

Figure 14:
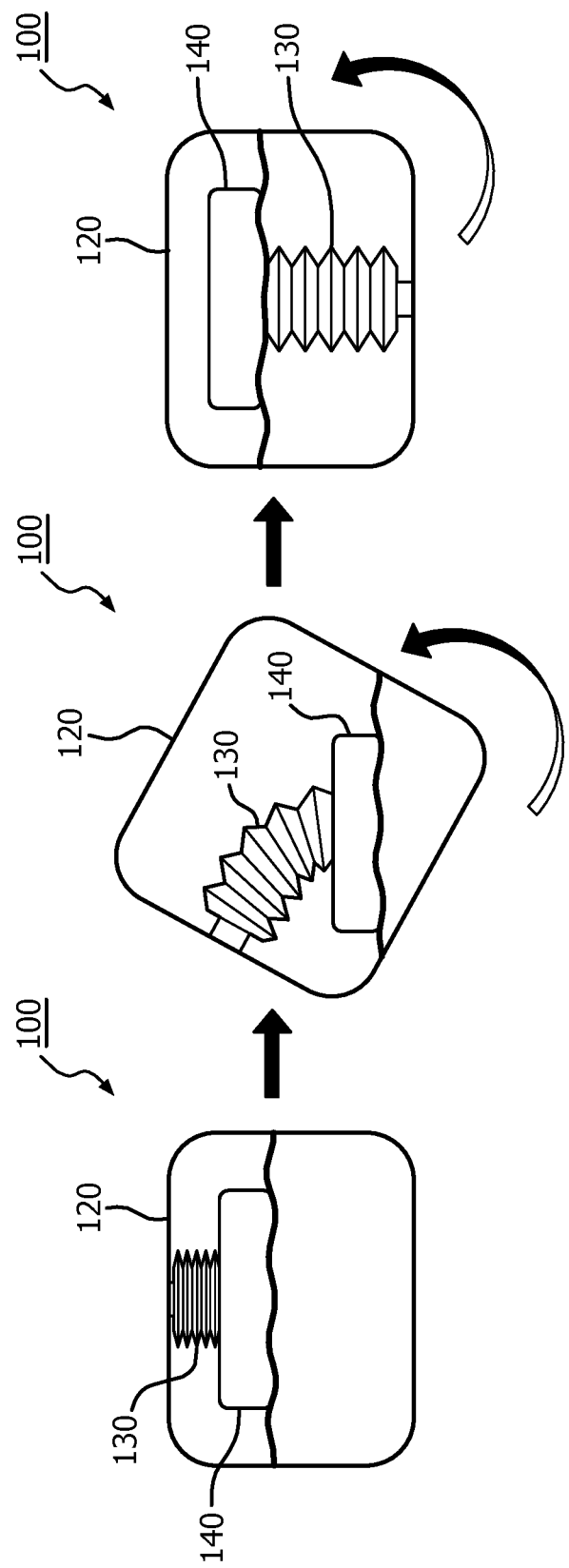

In addition, since float assembly 140 is adapted to float on top of the water within reservoir 120, apertures 153 will always be above the surface of the water, even during misuse conditions such as when humidifier assembly 100 is tilted or turned upside down by the user. Accordingly, water will advantageously be prevented from entering apertures 153 and passing to the main housing of pressure support system 50, as it will not be able to reach apertures 153. Water is also prevented from entering inlet end 111 of adaptor 110 through inlet port 112 because of the sealed connection between inlet port 112 and inlet tube 130. This is demonstrated schematically in FIG. 14.

Furthermore, because humidifier assembly 100 no longer needs to account for the potential of water ingress into the main housing of pressure support system 50 as just described, humidifier assembly 100 can advantageously be reduced in size.

The invention has been described in detail for the purpose of illustration based on what is currently considered to be the most practical exemplary embodiments. However, it is to be understood that such detail is solely for that purpose and that the invention is not limited to the disclosed embodiments, but, on the contrary, is intended to cover modifications and equivalent arrangements that are within the spirit and scope of the appended claims. For example and without limitation, although the disclosed concept has been described in association with a float assembly 140 that includes disc-shaped components 141, 149, it is within the scope of the disclosed concept for components of a float assembly to have alternative shapes, such as being rectangular-shaped, or to have a unitary float assembly (not shown) with a number of apertures therein for air to flow through. It is also within the scope of the disclosed concept for the inlet structure leading into reservoir 120 and the outlet structure leading out of the reservoir 120 to be located in positions other than on an adaptor as described herein. For example, and without limitation, one of both of the inlet structure and the outlet structure may be located on/in the side walls of reservoir 120 and/or on some structure, such as a lid or top wall, covering the top of reservoir 120.

Figure 15:
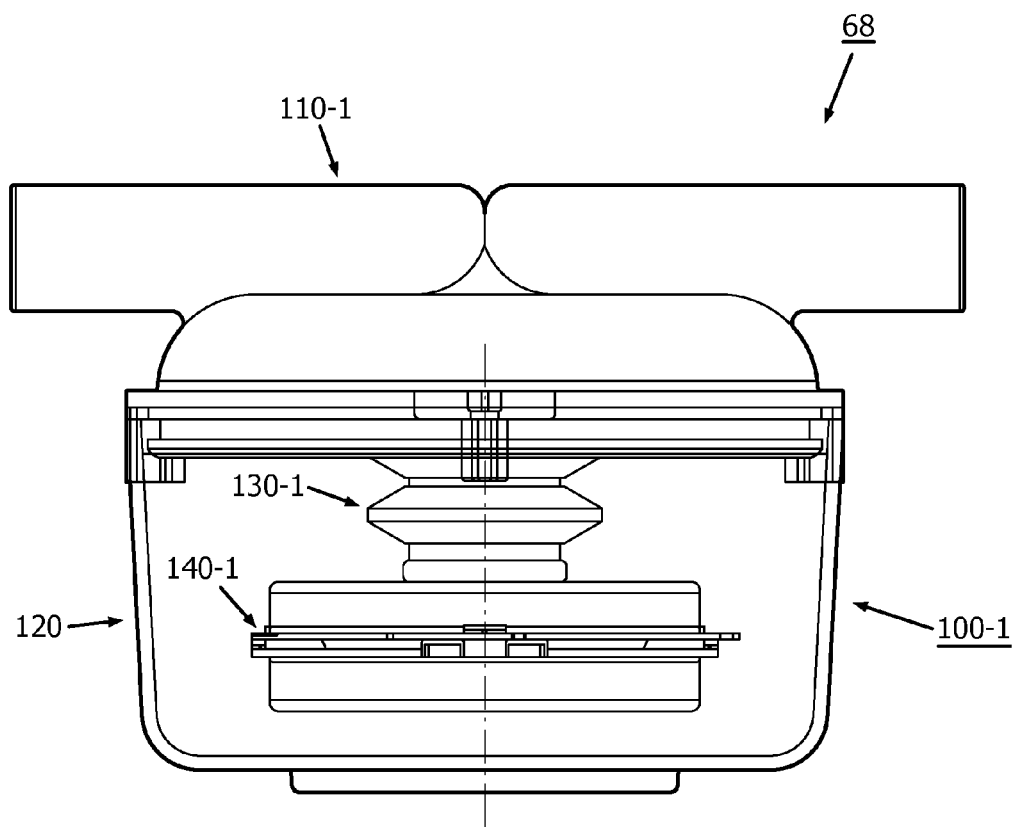
FIG. 15 is a front elevational view of another humidifier assembly in accordance with an alternative exemplary embodiment of the disclosed concept.
Figure 16:
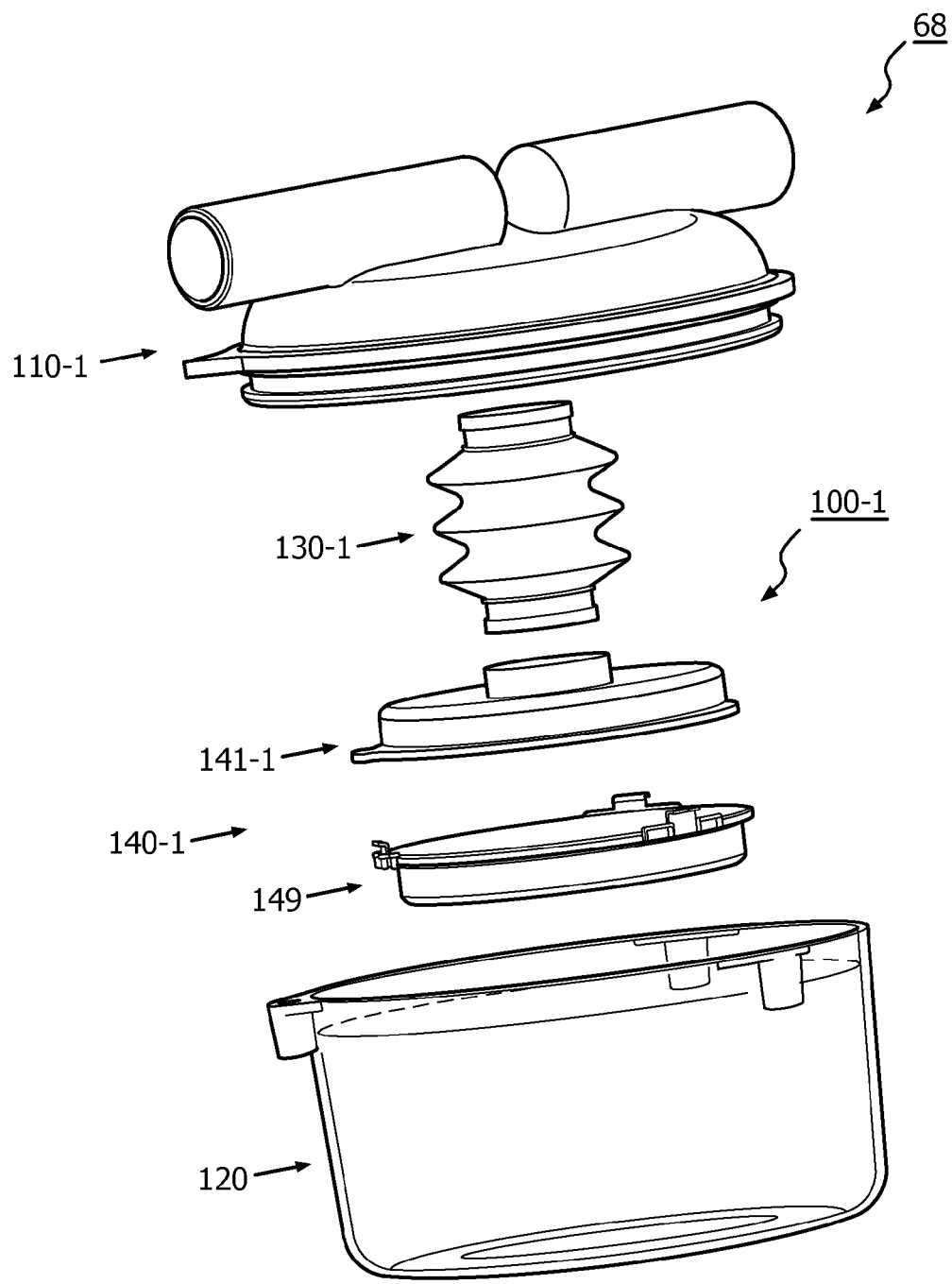
FIG. 16 is an exploded view of the humidifier assembly of FIG. 15.

FIG. 15 is a front elevational view and FIG. 16 is an exploded view of a humidifier assembly 100-1 according to an alternative exemplary embodiment of the present invention that may be used to implement humidifier 68 of pressure support system 50. Humidifier assembly 100-1 is similar to and includes many of the same components as humidifier assembly 100, and like components are labeled with like reference numerals. As seen in FIGS. 15 and 16, humidifier assembly 100-1 includes an adaptor 110-1, reservoir 120, a conduit 130-1, and a float assembly 140-1.

Figure 17:
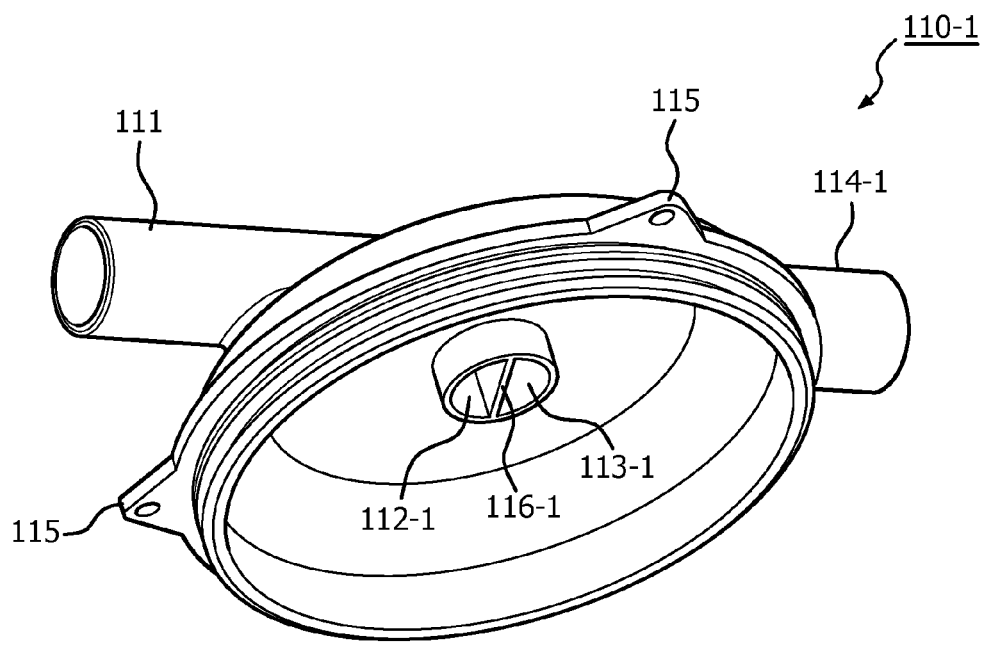
FIG. 17 is a bottom isometric view of an adaptor of the humidifier assembly of FIG. 15.

As seen in FIG. 17, adaptor 110-1 is similar to adaptor 110 (FIG. 4), including inlet end 111 through which breathing gas from gas flow generator 52 can enter humidifier assembly 100-1, and apertures 115 for coupling adaptor 110-1 to reservoir 120. However, adaptor 110-1 includes an inlet port 112-1 adjacent an outlet port 113-1, and an outlet end 114-1. Inlet port 112-1 is structured to be in fluid communication with inlet end 111 and outlet port 113-1 is structured to be in fluid communication with outlet end 114-1. Inlet port 112-1 and outlet port 113-1 are divided by a flow separator 116-1.

Figure 18:
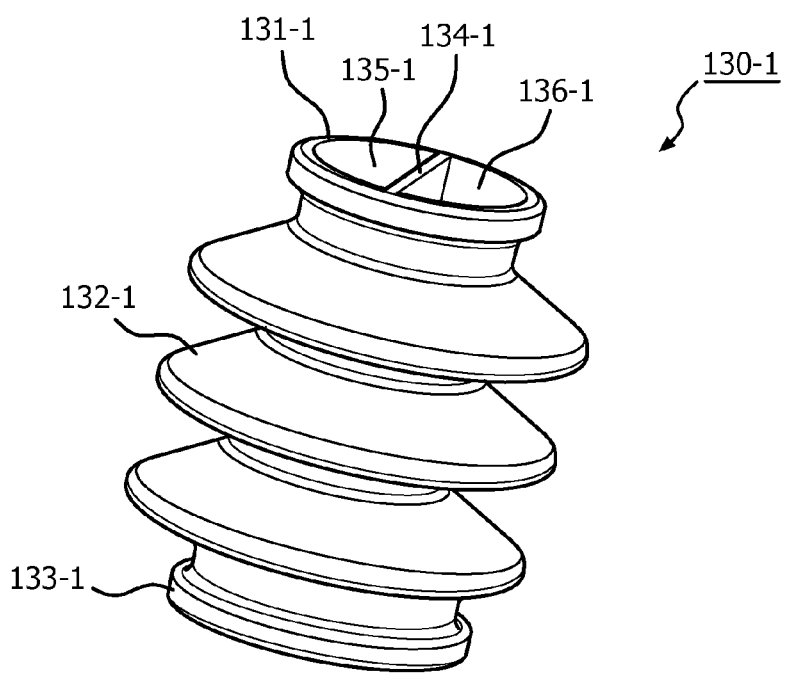
FIG. 18 is an isometric view of a conduit of the humidifier assembly of FIG. 15.
Figure 19:
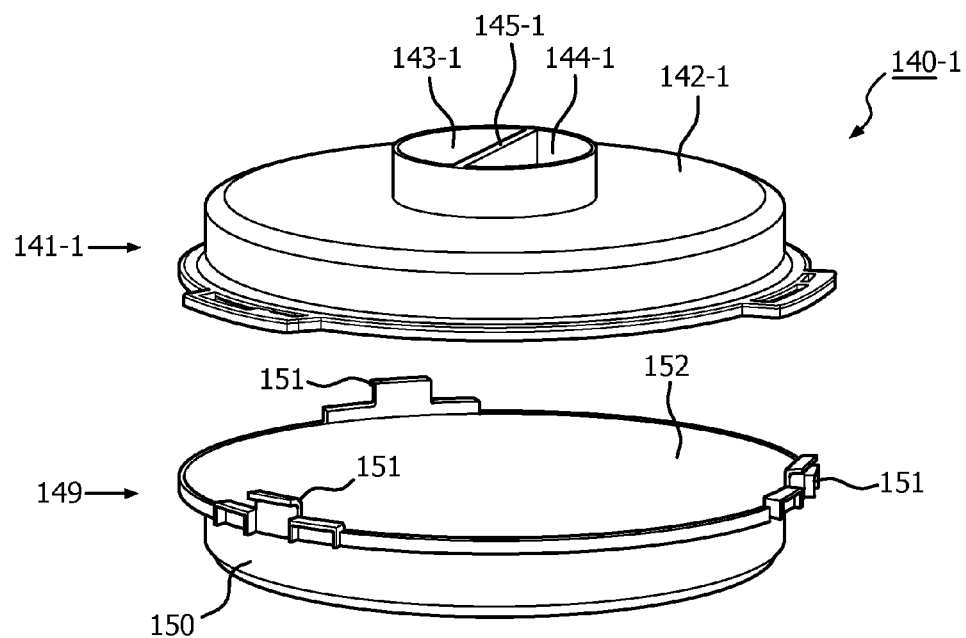
FIG. 19 is a partially exploded isometric view of a float assembly of the humidifier assembly of FIG. 15.

FIG. 18 is an isometric view of conduit 130-1. As seen, conduit 130-1 includes a first end 131-1 that is structured to be coupled to adaptor 110-1, a flexible body portion 132-1 similar to body portion 132 of inlet tube 130, and a second end 133-1 that is structured to be coupled to float assembly 140-1. Additionally, conduit 130-1 has an inlet passage 135-1 and an outlet passage 136-1 that are formed and deformed by a flow separator 134-1 extending longitudinally from first end 131-1 to second end 133-1. Flow separator 134-1 of conduit 130-1 aligns with flow separator 116-1 of adaptor 110-1 and operates to separate airflow into and out of conduit 130-1. In the non-limiting, exemplary embodiment, flow separator 134-1 is generally a thin elastomeric membrane that is less rigid than body portion 132-1. As a result, as body portion 132-1 expands, contracts, or otherwise moves during use, flow separator 134-1 advantageously maintains separation of inlet passage 135-1 and outlet passage 136-1 and thus separation of airflow into and out of conduit 130-1.

FIGS. 19-22 are exploded isometric views of float assembly 140-1. Float assembly 140-1 includes a first disc-shaped component 141-1 and, similar to float assembly 140 of humidifier assembly 100, includes second component 149. First component 141-1 has an enclosure piece 142-1 and a base 146-1 coupled to enclosure piece 142-1. Enclosure piece 142-1 includes an inlet port 143-1 and an outlet port 144-1, each coupled to second end 133-1 of conduit 130-1. Enclosure piece 142-1 further includes a flow separator 145-1 located between and separating inlet port 143-1 and outlet port 144-1. Flow separator 145-1 of enclosure piece 142-1 aligns with flow separator 134-1 of conduit 130-1 and operates to separate airflow into and out of float assembly 140-1. First component 141-1 further has a base 146-1 having a central aperture 147-1 and a flow separator 148-1 extending across central aperture 147-1 and thereby separating aperture 147-1 into inlet and outlet portions. Flow separator 148-1 of base 146-1 aligns with flow separator 145-1 of enclosure piece 142 and operates with flow separator 145-1 to separate airflow into and out of float assembly 140-1 into separate inlet and outlet paths.

Figure 20:
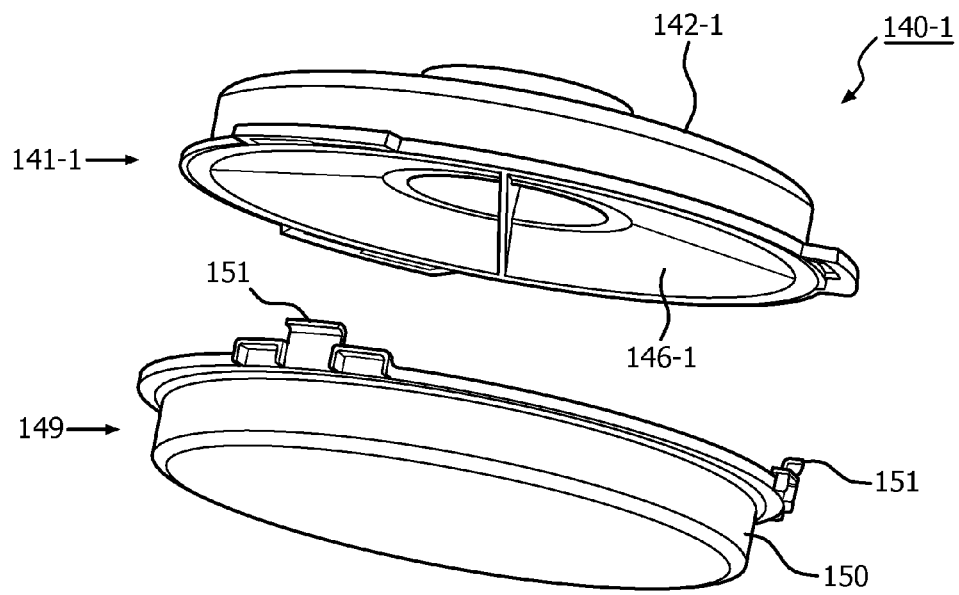
FIG. 20 is another partially exploded isometric view of the float assembly of the humidifier assembly of FIG. 15.
Figure 21:
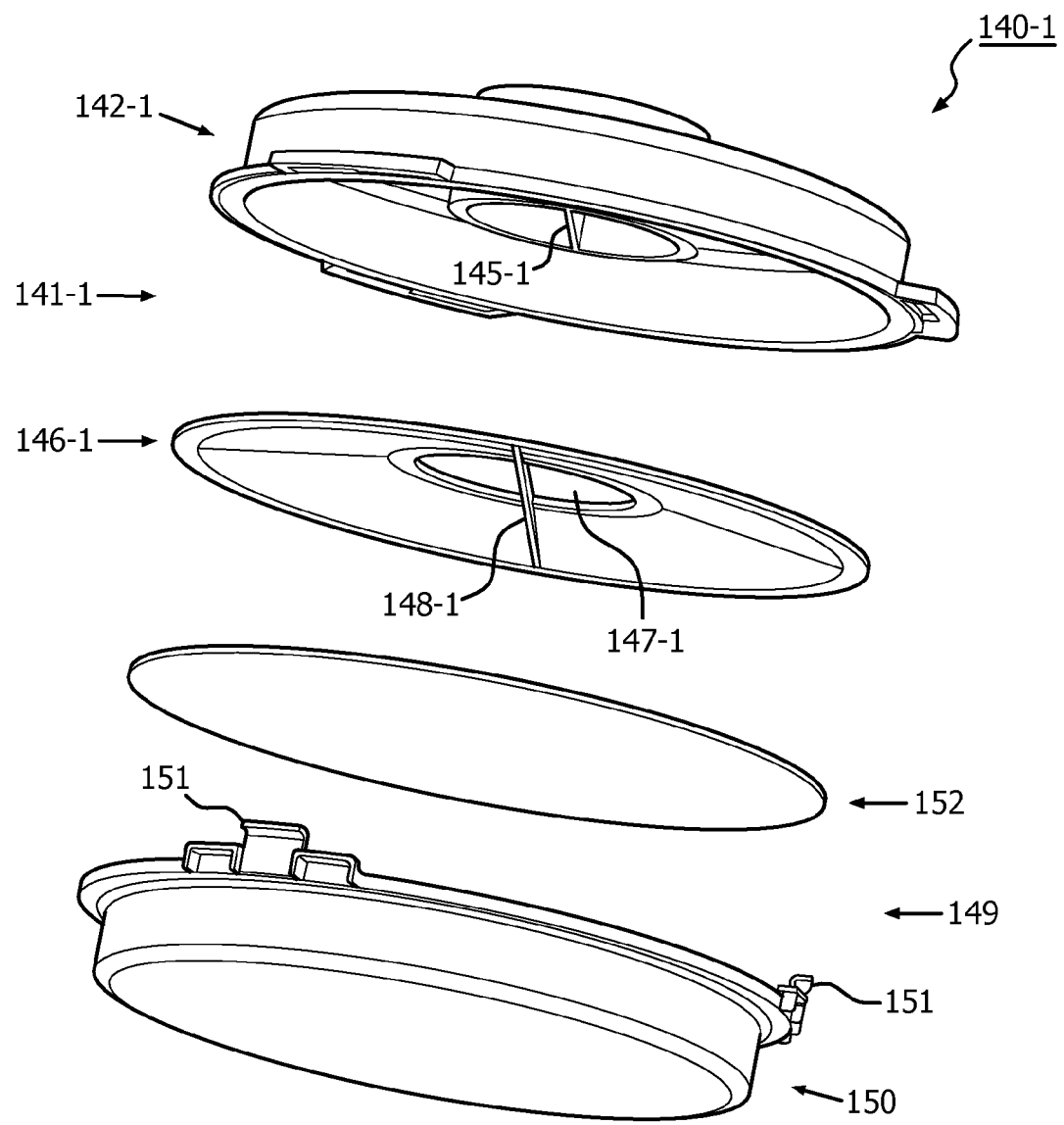
FIG. 21 is an exploded isometric view of the float assembly of the humidifier assembly of FIG. 15.
Figure 22:
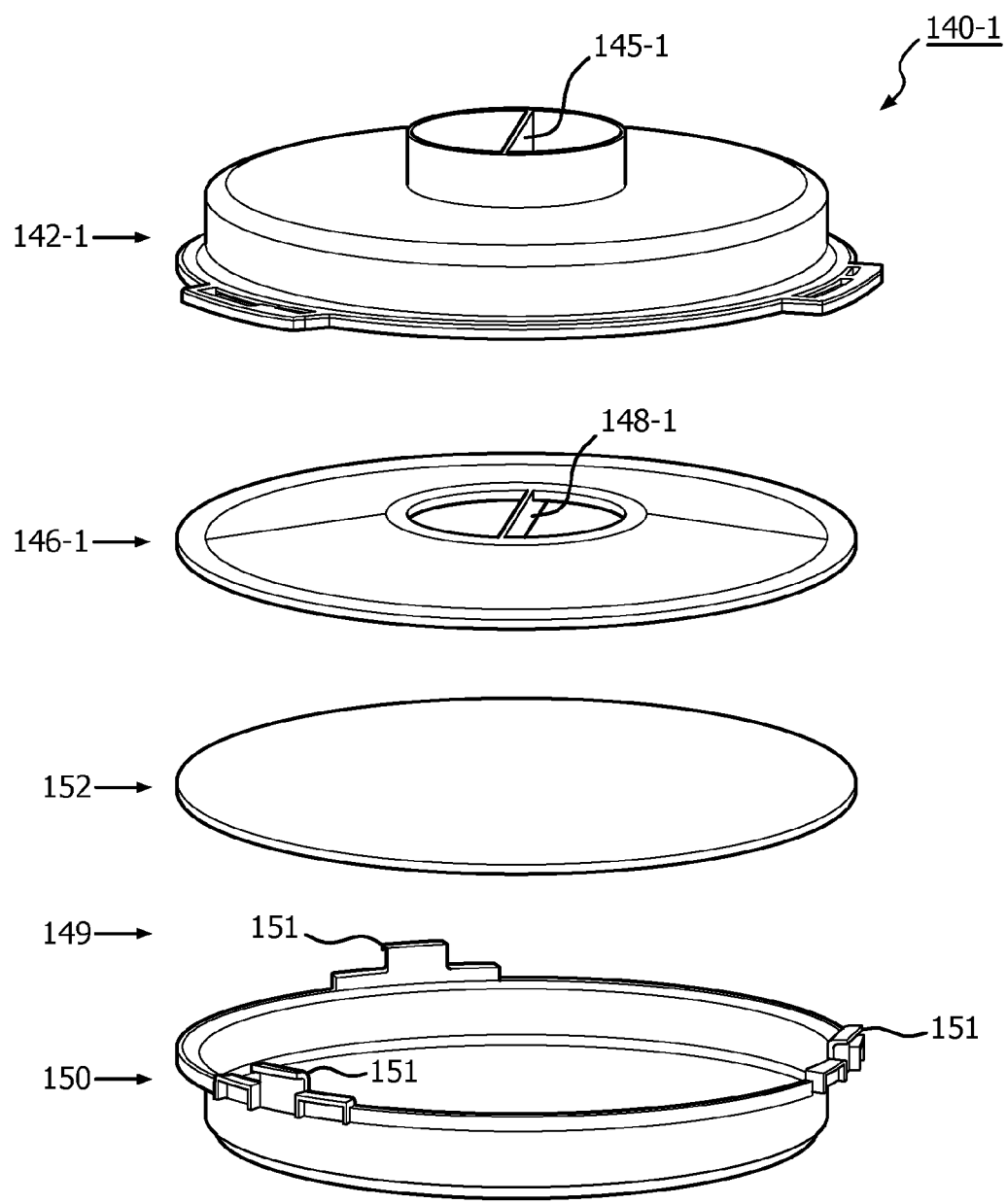
FIG. 22 is another exploded isometric view of the float assembly of the humidifier assembly of FIG. 15.

Additionally, as seen in FIGS. 20 and 21, flow separator 148-1 extends along the conical-shaped surface of base 146-1 from central aperture 147-1 to a peripheral edge of base 146-1. Flow separator 148-1 further extends from central aperture 147-1 at a first end and sealingly engages enclosure piece 152 at a second end. It will be appreciated that there is a gap between the peripheral edge of base 146-1 and enclosure piece 152. In this manner, airflow into and out of first component 141-1 is advantageously further separated along the sides of flow separator 148-1.

Figure 23:
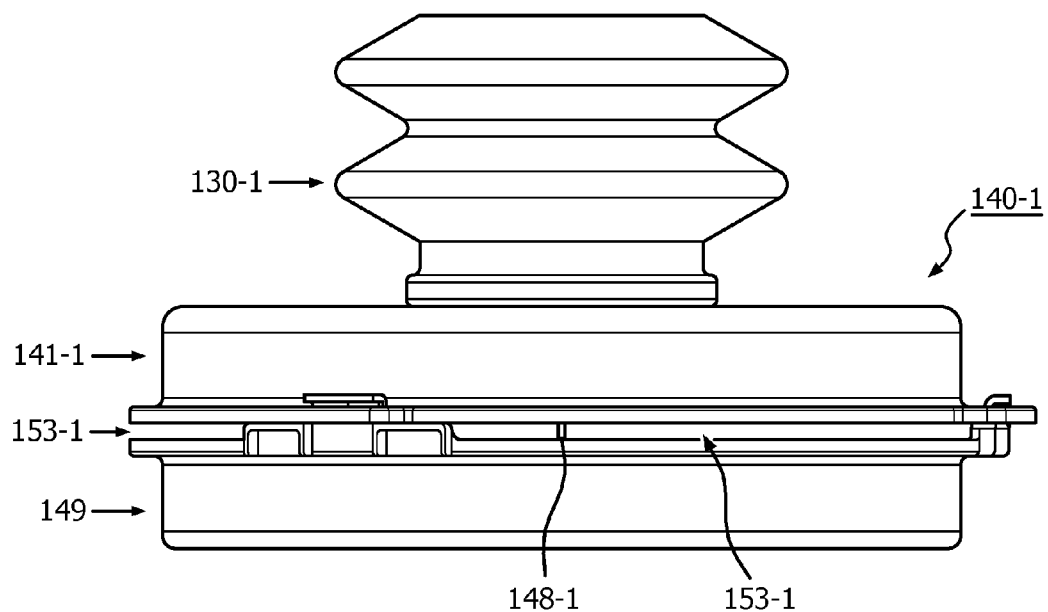
FIG. 23 is a front elevational view of the float assembly and a portion of the conduit of the humidifier assembly of FIG. 15.

FIG. 23 is a front elevational view showing conduit 130-1 coupled to float assembly 140-1. As seen in FIG. 23, when first component 141-1 of float assembly 140-1 is coupled to second component 149, a number of apertures 153-1 are formed therebetween. As described in more detail below, apertures 153-1 allow breathing gas from the inlet path to escape float assembly 140-1 and enter reservoir 120 for humidification, and also allow breathing gas to re-enter float assembly 140-1 once humidified. In the exemplary embodiment, three apertures 153-1 are formed.

In operation, breathing gas from gas flow generator 52 enters humidifier assembly 100-1 through inlet end 111 of adaptor 110-1. Breathing gas then flows through inlet port 112-1 and enters inlet passage 135-1 of conduit 130-1. The flow of gas is prevented from extending into outlet port 113-1 of adaptor 110-1 and outlet passage 136-1 of conduit 130-1 by flow separators 116-1, 134-1. The breathing gas enters float assembly 140-1 through inlet port 143-1 of first component 141-1 before passing through the inlet portion of central aperture 147-1 of base 146-1, at which point it is fanned out radially over enclosure piece 152. Flow separators 145-1 and 148-1 of float assembly 140-1 prevent the breathing gas coming from inlet passage 135-1 of conduit 130-1 from entering outlet passage 136-1 before being humidified.

The breathing gas enters reservoir 120 through apertures 153-1 and after being passed over water, is forced back through apertures 153-1 and into central aperture 147-1 of base 146-1 and outlet port 144-1 of enclosure piece 142-1. The breathing gas then passes into outlet passage 136-1 of conduit 130-1. Finally, the breathing gas is directed through outlet port 113-1 of adaptor 110-1 to outlet end 114-1 before being delivered to the patient. In this manner, inlet port 112-1 of adaptor 110-1, inlet passage 135-1 of conduit 130-1, and inlet port 143-1 of first component 141-1 form a first (inlet) flow path; and outlet port 113-1 of adaptor 110-1, outlet passage 136-1 of conduit 130-1, and outlet port 144-1 of first component 141-1 form a second (outlet) flow path. Flow separators 116-1, 134-1, 145-1, 148-1 advantageously operate to ensure that breathing gas passing through the first flow path does not enter the second flow path before entering the reservoir and also ensure that breathing gas passing through the second flow path does not enter the first flow path. In other words, only breathing gas that has been passed over water and thus humidified will exit humidifier assembly 100-1 and be delivered to the patient circuit.

Figure 24A:
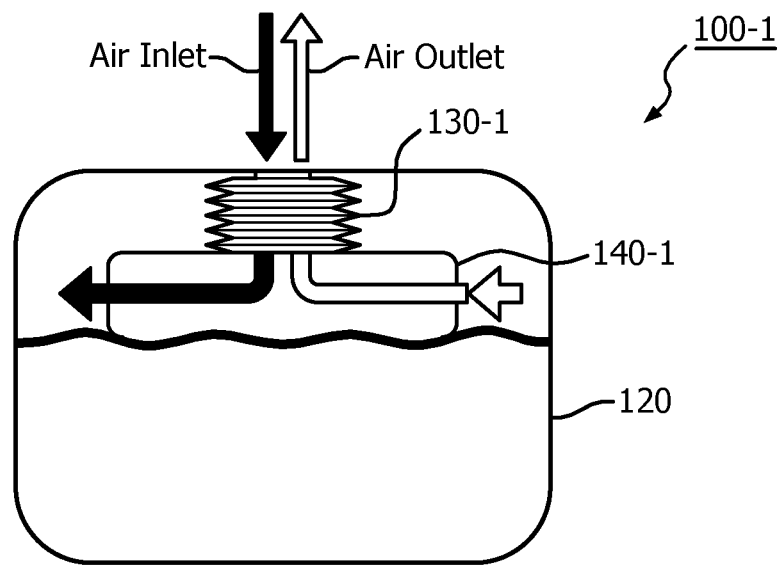
FIGS. 24A and 24B are schematic representations demonstrating operation of the humidifier assembly of FIG. 15.
Figure 24B:
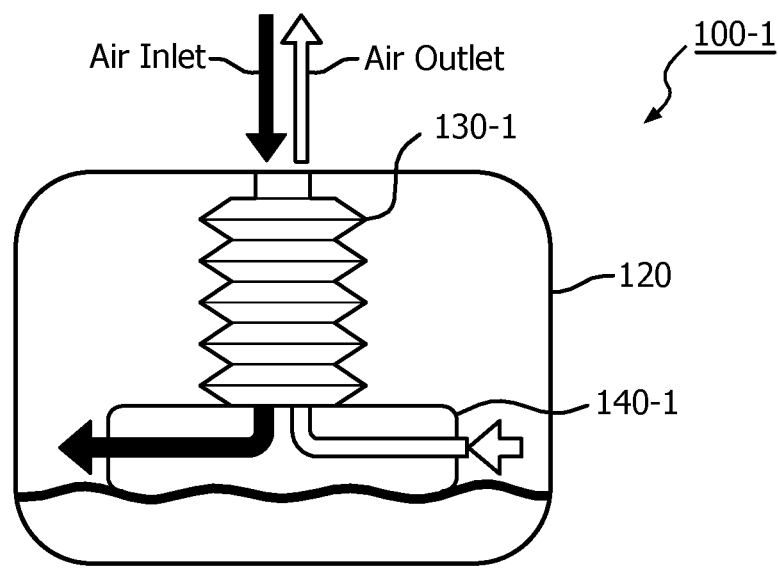

During use, float assembly 140-1, like float assembly 140, will remain at the same position with respect to the water level in reservoir 120 at all times. This is due to the fact that, as the water level in reservoir 120 changes, body portion 132-1 of conduit 130-1 will expand or contract, and/or bend, as needed as float assembly 140-1 floats on top of the water. In this manner, breathing gas will enter reservoir 120 through apertures 153-1 at the same level with respect to the water. This is demonstrated schematically in FIGS. 24A and 24B. This advantageously results in a more consistent humidification output being delivered to patient 54. Since float assembly 140-1 is adapted to float on top of the water within reservoir 120, apertures 153-1 (FIG. 23) will always be above the surface of the water, even during misuse conditions such as when humidifier assembly 100-1 is tilted or turned upside down by the user. Accordingly, because water will not be able to reach apertures 153-1, water will advantageously be prevented from entering apertures 153-1 and passing to the main housing of pressure support system 50 as well as be prevented from passing to the patient circuit.

Similar to humidifier assembly 100, humidifier assembly 100-1 has been described in detail for the purpose of illustration based on what is currently considered to be the most practical exemplary embodiments. However, it is to be understood that such detail is solely for that purpose and that the invention is not so limited but, on the contrary, is intended to cover modifications and equivalent arrangements that are within the spirit and scope of the appended claims. For example and without limitation, humidifier assembly 100-1, which operates to prevent water from flowing into the main housing of pressure support system 50 as well as to the patient circuit, has been described in association with adaptor 110-1, conduit 130-1, and float assembly 140-1. A suitable alternative humidifier assembly (not shown) within the scope of the disclosed concept includes an inlet tube having an outlet tube located within the inlet tube (a so called "tube within a tube" configuration). An adaptor and a float assembly corresponding to such an implementation would include flow separators generally aligning with a cross sectional profile of the outlet tube located within the inlet tube. Additionally, it is also within the scope of the disclosed concept for a humidifier assembly (not shown) to include an inlet tube located within an outlet tube, and corresponding adaptor and float assembly to include flow separators generally aligning with the cross sectional profile of the inlet tube located within the outlet tube.

Additional implementations which operate to prevent water from flowing into the main housing of pressure support system 50 as well as the patient circuit are not limited to inlet portions directly adjacent outlet portions. For example and without limitation, it is within the scope of the disclosed concept for a humidifier assembly (not shown) to include an inlet tube spaced apart from a separate outlet tube. A corresponding adaptor and float assembly would include separate ports spaced apart to couple to the corresponding inlet and outlet tubes. Additionally, it is within the scope of the disclosed concept for such an implementation to include a separate float assembly for each of the inlet and outlet tubes.

What is claimed is:

1. A humidifier assembly, comprising:
a reservoir structured to hold water;
an inlet structure leading into the reservoir and an outlet structure leading out of the reservoir, the inlet structure being structured to receive a flow of breathing gas;
a conduit element having a first end, a body portion, and a second end, the first end being fluidly coupled to at least one of the inlet structure and the outlet structure;
a float assembly coupled to the second end of the conduit element and being structured to float on the water held by the reservoir, the float assembly having a number of apertures structured to be in fluid communication with an interior of the reservoir and the outlet structure;
wherein each of the number of apertures are structured to be positioned above a surface of the water regardless of an orientation of the reservoir, and
wherein the body portion is a flexible body portion and has a bellows shape.

2. The humidifier assembly according to claim 1, further comprising an adaptor coupled to the reservoir and having an inlet end, an inlet port coupled to the inlet end, the inlet port comprising the inlet structure, and an outlet end comprising the outlet structure.

3. The humidifier assembly according to claim 1, wherein the conduit element comprises an inlet tube having a single flow passage; wherein the first end is directly coupled to the inlet structure but not directly coupled to the outlet structure.

4. The humidifier assembly according to claim 1, further comprising an adaptor coupled to the reservoir, the adaptor having an inlet port, an outlet port, and a first flow separator disposed between the inlet port and the outlet port, the inlet port being part of the inlet structure and the outlet port being part of the outlet structure; wherein the first end of the conduit element is fluidly coupled to the inlet port and the outlet port.

5. The humidifier assembly according to claim 4, wherein the conduit element further has an inlet passage, an outlet passage, and a second flow separator therebetween, the second flow separator extending from the first end to the second end and being aligned with the first flow separator.

6. The humidifier assembly according to claim 5, wherein the float assembly comprises a first component and a second component coupled to the first component, the apertures of the float assembly being disposed between the first component and the second component, wherein the first component includes an inlet port, an outlet port, and a third flow separator disposed therebetween and being aligned with the second flow separator.

7. The humidifier assembly according to claim 6, wherein the inlet port of the adaptor, the inlet passage of the conduit element, and the inlet port of the first component form a first flow path; wherein the outlet port of the adaptor, the outlet passage of the conduit element, and the outlet port of the first component form a second flow path; wherein the first, second, and third flow separators are structured to prevent the breathing gas passing through the first flow path from entering the second flow path before entering the reservoir; and wherein the first, second, and third flow separators are further structured to prevent the breathing gas passing through the second flow path from entering the first flow path.

8. The humidifier assembly according to claim 1, wherein the conduit element includes an inlet passage and an outlet passage separate from the inlet passage; wherein the inlet passage is fluidly coupled to the inlet structure and the number of apertures; and wherein the outlet passage is fluidly coupled to the outlet structure and the number of apertures.

9. A pressure support system, comprising:
the humidifier assembly according to claim 1;
a gas flow generator coupled to the inlet structure, the gas flow generator being structured to produce the flow of breathing gas; and
a patient interface coupled to the outlet structure, the patient interface being structured to communicate the flow of breathing gas to an airway of a patient.

10. A humidifier assembly, comprising:
a reservoir structured to hold water;
an inlet structure leading into the reservoir and an outlet structure leading out of the reservoir, the inlet structure being structured to receive a flow of breathing gas;
a conduit element having a first end, a body portion, and a second end, the first end being fluidly coupled to at least one of the inlet structure and the outlet structure;
a float assembly coupled to the second end of the conduit element and being structured to float on the water held by the reservoir, the float assembly having a number of apertures structured to be in fluid communication with an interior of the reservoir and the outlet structure;
wherein each of the number of apertures are structured to be positioned above a surface of the water regardless of an orientation of the reservoir, and
wherein the float assembly comprises a first component and a second component coupled to the first component, the apertures of the float assembly being disposed between the first component and the second component.

11. The humidifier assembly according to claim 10, wherein the second component has a top surface structured to act as a baffle to radially disperse the breathing gas passing through the second end of the conduit element and out the number of apertures.

12. A method of providing moisture to supplied gas in a pressure support system, the method comprising the steps of:
generating a flow of breathing gas with a gas flow generator, the gas flow generator adapted to be coupled to a humidifier assembly, the humidifier assembly comprising a reservoir adapted to contain water, a conduit element and a float assembly coupled to the conduit element and having a number of apertures, the float assembly being adapted to float on the water, each of the number of apertures being structured to be positioned above a surface of the water regardless of an orientation of the reservoir;
passing the breathing gas through the conduit element and through the number of apertures of the float assembly;
passing the breathing gas over the water; and
delivering the breathing gas from the humidifier assembly to a patient via a patient circuit coupled to the reservoir.

13. The method according to claim 12, wherein the conduit element is an inlet tube having a single flow passage, and wherein the delivering comprises delivering the breathing gas to the patient circuit through a flow path not forming part of the conduit element.

14. The method according to claim 12, wherein the conduit element comprises a first flow passage and a second flow passage, wherein the passing the breathing gas through the conduit element comprises passing the breathing gas through the first flow passage, and wherein the delivering comprises delivering the breathing gas to the patient circuit through a flow path including the second flow passage.

* * * * *